US010911646B2

(12) United States Patent
Ouyang

(10) Patent No.: US 10,911,646 B2
(45) Date of Patent: Feb. 2, 2021

(54) ORAL ENDOSCOPE

(71) Applicant: Beijing keeyoo Technologies Co., Ltd., Beijing (CN)

(72) Inventor: Congxing Ouyang, Beijing (CN)

(73) Assignee: BEIJING KEEYOO TECHNOLOGIES CO., LTD., Beijing (CN)

( * ) Notice: Subject to any disclaimer, the term of this patent is extended or adjusted under 35 U.S.C. 154(b) by 0 days.

(21) Appl. No.: 16/617,896

(22) PCT Filed: May 17, 2018

(86) PCT No.: PCT/CN2018/087392
§ 371 (c)(1),
(2) Date: Nov. 27, 2019

(87) PCT Pub. No.: WO2018/219157
PCT Pub. Date: Dec. 6, 2018

(65) Prior Publication Data
US 2020/0169649 A1 May 28, 2020

(30) Foreign Application Priority Data

May 27, 2017 (CN) .......................... 2017 1 0393180
Nov. 24, 2017 (CN) .......................... 2017 1 1195257

(51) Int. Cl.
*H04N 13/00* (2018.01)
*H04N 7/18* (2006.01)
(Continued)

(52) U.S. Cl.
CPC ....... *H04N 5/2252* (2013.01); *A61B 1/00009* (2013.01); *A61B 1/00016* (2013.01);
(Continued)

(58) Field of Classification Search
CPC .. H04N 5/2252; H04N 13/239; H04N 13/246; H04N 13/296; H04N 13/194;
(Continued)

(56) References Cited

U.S. PATENT DOCUMENTS

2004/0097805 A1* 5/2004 Verard ............... A61B 1/00071
600/428
2012/0163656 A1* 6/2012 Wang ........................ G06T 7/73
382/103
(Continued)

FOREIGN PATENT DOCUMENTS

CN 103040429 A 4/2013
CN 104349710 A 2/2015
(Continued)

*Primary Examiner* — Sherrie Hsia
(74) *Attorney, Agent, or Firm* — Harness, Dickey & Pierce, P.L.C.

(57) ABSTRACT

The present application relates to the technical field of oral care devices, and discloses an oral endoscope, the oral endoscope comprising: a housing; an image acquisition module, which is fixedly mounted within the housing and which is used for acquiring an external image through the housing, the image acquisition module comprising at least two camera units, which are relatively positionally calibrated and which are used for acquiring three-dimensional image information; an illuminating unit, which provides illumination for each camera unit; a wireless communications module, which is used for wirelessly communicating with an external device and for sending image information, which is acquired by the image acquisition module, to the external device. The oral endoscope may acquire three-dimensional images at various positions in an oral cavity; the oral endoscope need not scan various positions in the oral cavity according to a set sequential requirement, thus
(Continued)

the operational requirements thereof are low, and the present invention may be used for self-serviced dentition molding by an ordinary user.

21 Claims, 10 Drawing Sheets

(51) Int. Cl.
| | |
|---|---|
| *H04N 5/225* | (2006.01) |
| *H04N 13/246* | (2018.01) |
| *H04N 13/194* | (2018.01) |
| *H04N 13/239* | (2018.01) |
| *A61B 1/00* | (2006.01) |
| *A61B 1/05* | (2006.01) |
| *A61B 1/06* | (2006.01) |
| *A61B 1/24* | (2006.01) |

(52) U.S. Cl.
CPC ...... *A61B 1/00029* (2013.01); *A61B 1/00057* (2013.01); *A61B 1/00059* (2013.01); *A61B 1/00064* (2013.01); *A61B 1/05* (2013.01); *A61B 1/0661* (2013.01); *A61B 1/24* (2013.01); *H04N 13/194* (2018.05); *H04N 13/239* (2018.05); *H04N 13/246* (2018.05); *H04N 2005/2255* (2013.01)

(58) Field of Classification Search
CPC ............ H04N 7/183; H04N 2005/2255; A61B 1/00009; A61B 1/00016; A61B 1/00029; A61B 1/00057; A61B 1/00059; A61B 1/00064; A61B 1/05; A61B 1/06; A61B 1/042; A61B 1/045; A61B 1/04; A61B 1/005; A61B 1/0661; A61B 1/24
USPC .................................. 348/45, 47, 48, 65, 66
See application file for complete search history.

(56) References Cited

U.S. PATENT DOCUMENTS

| | | | |
|---|---|---|---|
| 2014/0146142 A1* | 5/2014 | Duret | ................ A61B 1/00158 348/47 |
| 2014/0272764 A1 | 9/2014 | Miller et al. | |
| 2016/0262856 A1 | 9/2016 | Atiya et al. | |

FOREIGN PATENT DOCUMENTS

| | | |
|---|---|---|
| CN | 106618466 A | 5/2017 |
| CN | 107295227 A | 10/2017 |
| WO | WO-2016113745 A1 | 7/2016 |

\* cited by examiner

ORAL ENDOSCOPE

The present application claims priority to Chinese patent application No. 201710393180.8 filed with China Patent Office on May 27, 2017 and entitled "DENTAL ENDOSCOPE" and Chinese patent application No. 201711195257.7 filed with China Patent Office on Nov. 24, 2017 and entitled "DENTAL ENDOSCOPE", the contents of each of which are incorporated herein by reference in its entirety.

FIELD

The present application relates to the technical field of dental medical equipment, in particular to a dental endoscope.

BACKGROUND

A traditional dental endoscope is a device used for dental impression. This device requires an optical tip to respectively slide on an upper dentition and a lower dentition of a user, to complete optical impression of a complete dentition. An existing dental endoscope is only provided with one camera unit, and only one piece of image information can be acquired during each image capturing moment. During tooth impression operation of the dental endoscope, an upper and a lower dentition should be scanned in sequence from each angle according to a set sequence and requirement, so as to facilitate follow-up three-dimensional synthesis of a dentition model, the operation requirement is relatively high, the specialization is very strong, and a professional is generally required for operation, therefore, user's self-service impression is difficult to realize.

SUMMARY

The present application discloses a dental endoscope, to provide a dental endoscope which can support self-service dentition impression operation of a user.

To achieve the above object, the present application provides the following technical solution.

A dental endoscope, including:

a housing;

an image acquisition module fixedly installed in the housing and configured to acquire an external image through the housing, where the image acquisition module includes at least two camera units with relative positions of which are calibrated and which are configured to acquire three-dimensional image information, and an illumination unit configured to provide illumination to each camera unit; and a wireless communication module, configured to perform wireless communication with an external device and send image information acquired by the image acquisition module to the external device.

In the above dental endoscope, the image acquisition module is arranged in the housing, and can acquire an external image through the housing, therefore, through arranging the housing in an oral cavity of a user, the image acquisition module in the housing can be utilized to acquire image information of the oral cavity of the user; since in the image acquisition module of the dental endoscope, each camera unit can acquire three-dimensional image information, that is, a three-dimensional image at respective position of the oral cavity can be acquired through the dental endoscope; further, images acquired by the dental endoscope can be directly used to form a digital model of complete dentition; moreover, since the dental endoscope includes at least two camera units, and relative positions of the at least two camera units are calibrated, thus, the image acquisition module can simultaneously acquire at least two three-dimensional images during each image capturing moment, and the at least two three-dimensional images can be used as a reference to each other, to determine angle and position information of each image capturing; therefore, the dental endoscope does not need to scan a tooth image according to a preset sequence, the operation requirement is relatively low, and can be applicable for ordinary users to take dentition impression by themselves.

In addition, since the dental endoscope is provided with a wireless communication module, the dental endoscope can send an acquired three-dimensional image to the external device, such as a smart phone, to perform such processing as synthesis and display of a digital model of complete dentition, and further facilitate a user to acquire a three-dimensional model of teeth at any time, and know conditions of teeth.

Optionally, each camera unit includes two cameras with relative positions of which are calibrated.

Optionally, each camera unit includes a camera array composed of multiple cameras with relative positions of which are calibrated.

Optionally, each camera unit includes a light field camera.

Optionally, the light field camera includes a front-end master lens and a rear-end photoreceptor, where the front-end master lens is a microlens array composed of multiple microlenses.

Optionally, the light field camera includes a front-end master lens and a rear-end photoreceptor, and a microlens array arranged between the front-end master lens and the rear-end photoreceptor and composed of multiple microlenses.

Optionally, the image acquisition module further includes surface structured light projection units which are in one-to-one correspondence with the camera units.

Optionally, the housing is ellipsoid-shaped, or cylinder-shaped with end faces at two ends being camber surfaces, or rounded-corner-column-shaped with end faces at two ends being camber surfaces.

Optionally, the housing includes two end faces arranged oppositely, and a side face arranged between two end faces; and the side face is composed of two first side faces arranged oppositely and two second side faces arranged oppositely; and the image acquisition module includes two pairs of first camera units, and the two pairs of first camera units are symmetrically arranged at two end parts, at a long axis direction, of the housing; where two first camera units in each pair of first camera units are arranged back to back, and cameras of the two first camera units respectively face towards two first side faces of the housing.

Optionally, the image acquisition module further includes two second camera units, and the two camera units are distributed in a cross section of the housing in which a center of the housing is located; and the two second camera units are arranged back to back, and cameras of the two second camera units respectively face towards two second side faces of the housing.

Optionally, the image acquisition module further includes two third camera units which are symmetrically arranged at two end parts, at a long axis direction, of the housing; and the two third camera units are arranged back to back, and cameras of the two third camera units respectively face towards two end faces of the housing.

Optionally, the dental endoscope further includes:

a storage module, configured to store image information acquired by the image acquisition module; and a master control module, which is respectively in signal connection with the image acquisition module, the storage module and the wireless communication module, and configured to control each camera unit to synchronously expose and synchronously acquire three-dimensional image information, send acquired three-dimensional image information to the storage module, and transmit image information stored by the storage module to the wireless communication module.

Optionally, the master control module is further configured to receive image information acquired by the image acquisition module, at least add corresponding timestamp information of image acquisition and identification of camera units to the image information, and send image information after adding to the storage module for storage.

Optionally, the dental endoscope further includes:

a power supply module, which is electrically connected with the image acquisition module, the wireless communication module, the master control module and the storage module, and configured to supply power to the image acquisition module, the wireless communication module, the master control module and the storage module;

a switch module, configured to control on and off states of a circuit by which the power supply module supplies power to each electric module; and the switch module includes a magnetic switch unit.

Optionally, the dental endoscope further includes a wireless charging module.

Optionally, the housing includes a probe part and a handheld part.

Optionally, the probe part and the handheld part are of an integrated structure.

Optionally, the image acquisition module is arranged in the probe part.

Optionally, the image acquisition module includes two camera units which are arranged back to back, and two illumination units which respectively provide illumination to the two camera units.

Optionally, the wireless communication module, the master control module and the storage module are all arranged in the handheld part.

Optionally, the dental endoscope further includes a base which is arranged to be independent of the housing;

where the base is provided with a magnetic switch driving module configured to drive the magnetic switch unit to perform on and off actions and a wireless power transmission module in match with the wireless charging module.

Optionally, the dental endoscope further includes:

a stretching part, arranged outside the housing, with one end being connected with the housing; where the stretching part includes a connector with one end being connected with the housing, and a handle connected with the other end of the connector.

Optionally, the connector is a drawstring or a connecting rod.

Optionally, the wireless communication module, the master control module, the storage module, the power supply module, the switch module and the wireless charging module are all arranged in the handle;

the connector includes an electrical connecting line; and the image acquisition module and the modules in the handle perform data communication and power transmission through the electrical connecting line.

Optionally, the master control module is further configured to:

send a handshake message to the external device through the wireless communication module according to a first preset period, and determine that a response message of handshake message returned by the external device is received within a first preset time duration, where the handshake message at least includes device identification of the dental endoscope; and the master control module is further configured to receive a user authentication passed message sent by the external device, where the user authentication passed message is sent by the external device when the external device determines that user authentication has passed according to device identification of the dental endoscope in the handshake message and a mapping relationship between the device identification and user identity.

DETAILED DESCRIPTION OF EMBODIMENTS

Figure 1:
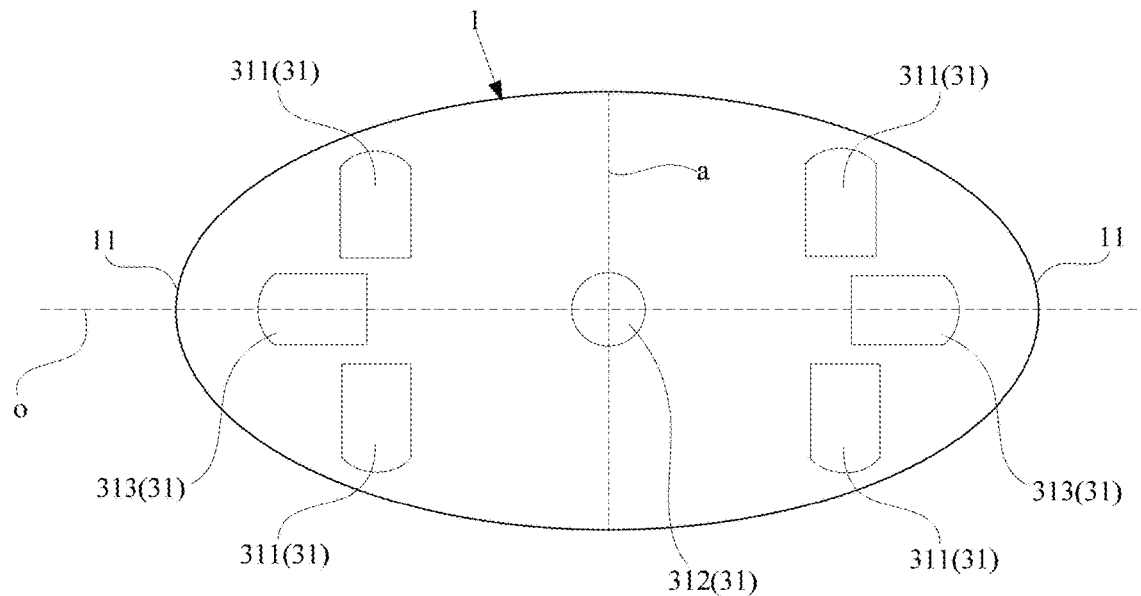
FIG. 1 is a structural schematic diagram of a dental endoscope when viewed from a second side of a housing of the dental endoscope provided by an embodiment of the present application.
Figure 2:
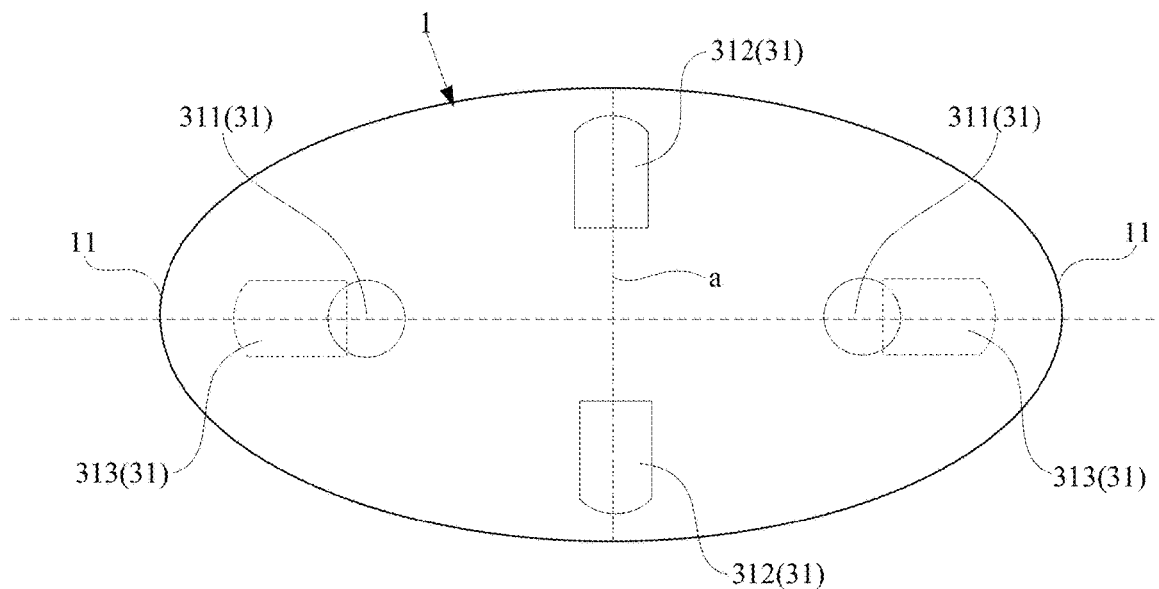
FIG. 2 is a structural schematic diagram of the dental endoscope in FIG. 1 when viewed from a first side of the housing of the dental endoscope.
Figure 3:
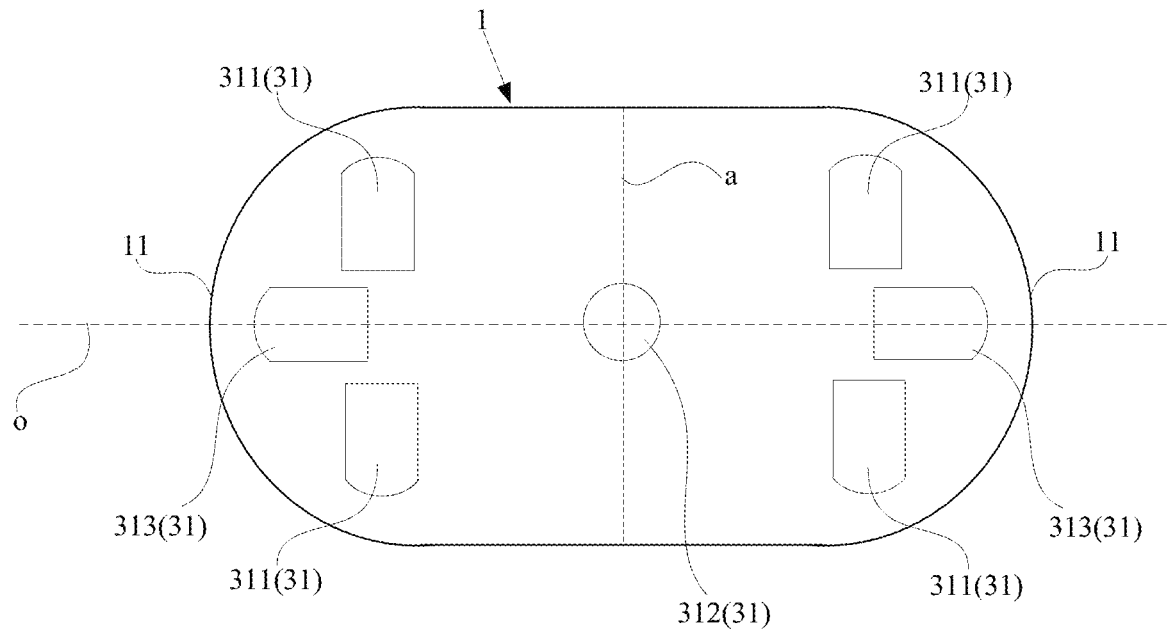
FIG. 3 is a structural schematic diagram of a dental endoscope when viewed from a second side of a housing of the dental endoscope provided by another embodiment of the present application.
Figure 4:
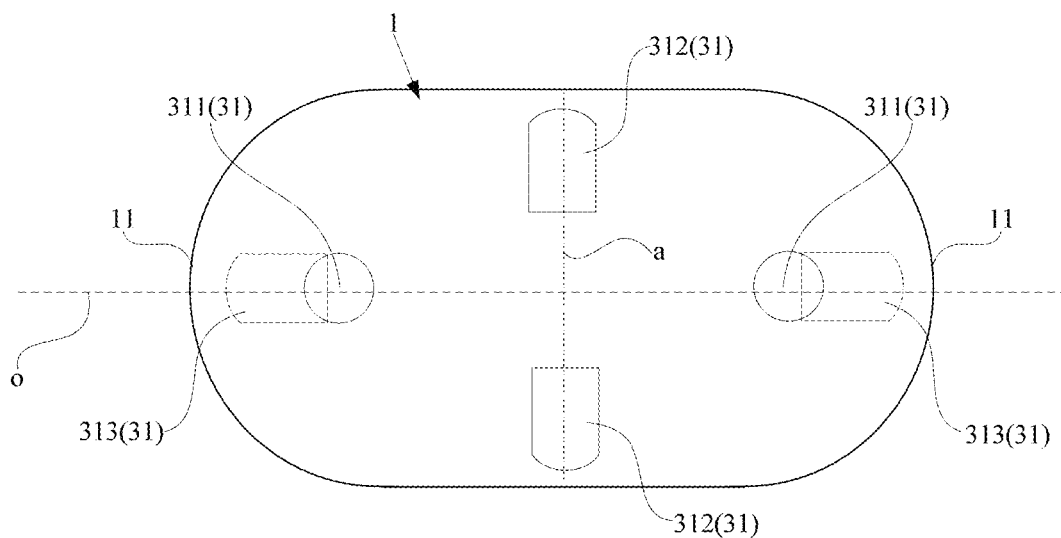
FIG. 4 is a structural schematic diagram of the dental endoscope in FIG. 3 when viewed from a first side of the housing of the dental endoscope.

In recent years, some self-service dental endoscopes are available for users. However, the use experience of these endoscopes is poor, and the main reasons are as follows: 1) due to a lack in three-dimensional image information, it is impossible to take a complete dentition impression, and a current digital model of the complete dentition cannot be generated in real time, therefore, professional applications in dentistry, such as orthodontics, dental restoration, dental implant, crown-type tooth cleaning device and 3D printing cannot be supported; 2) only one small partial picture can be acquired each time, and the position of the detail currently seen in an oral cavity can not be known; and 3) a user would be very tired since the mouth has to be opened for a long time.

A clear and complete description of the technical solution of embodiments of the present application will be given below in combination with the accompanying drawings in embodiments of the present application. Obviously, the described embodiments are only a part, but not all, of the embodiments of the present application. Based on the embodiments of the present application, all the other embodiments obtained by those of ordinary skill in the art without any creative effort shall all fall into the protection scope of the present application.

Please refer to FIG. 1 to FIG. 18.

As shown in FIG. 1 to FIG. 6, FIG. 16 and FIG. 17, the embodiments of the present application provide a dental endoscope, including:

a housing 1, and the housing 1 is a seal structure in which a confined space is formed;

an image acquisition module 3 fixedly installed in the housing 1 and configured to acquire an external image through the housing 1, and the image acquisition module 3 includes at least two camera units 31 and an illumination unit which provides illumination to the at least two camera units 31; where relative positions of the at least two camera units 31 are calibrated, that is, relative positions of the at least two camera units 31 are calibrated as internal parameters of the image acquisition module 3; and each camera unit 31 can acquire three-dimensional image information, that is, each camera unit 31 can acquire depth information of a subject; and a wireless communication module 41 configured to perform wireless communication with an external device and send image information acquired by an image acquisition module 3 to the external device.

In the above dental endoscope, the image acquisition module 3 is arranged in the housing 1, and acquires an external image through the housing 1; therefore, the image acquisition module 3 in the housing 1 can be used to acquire image information of an oral cavity of a user by placing the housing 1 in the oral cavity of the user. Each camera unit 31 in the image acquisition module 3 of the dental endoscope can acquire depth information of the subject, that is, a three-dimensional image of teeth can be acquired by the dental endoscope of the present application, therefore, an image acquired by the dental endoscope can be directly used to form a digital model of complete dentition, and further support a 3D digital impression taking in dental applications as orthodontics, dental restoration, dental implant, crown-type tooth cleaning device and 3D printing. The dental endoscope includes at least two camera units 31, and relative positions of the at least two camera units 31 are calibrated, the image acquisition module 3 can simultaneously acquire at least two three-dimensional images at each image capturing moment, and the at least two three-dimensional images can be taken as a reference to each other to determine position information in each image capturing operation, thus the dental endoscope is not required to perform image scanning according to a set sequence, and the operation requirement of which is relatively low, and can be applicable for ordinary users to take dentition impression by themselves.

In addition, the dental endoscope is provided with the wireless communication module 41, therefore, the dental endoscope can send an acquired three-dimensional image to the external device, to perform such processing as synthesis and display of a digital model of complete dentition, and further facilitate a user to acquire his three-dimensional tooth model at any time, and know conditions of his teeth.

In a particular embodiment, for each camera unit 31 in an image acquisition module 3, there are several specific embodiments as follows.

Figure 8:
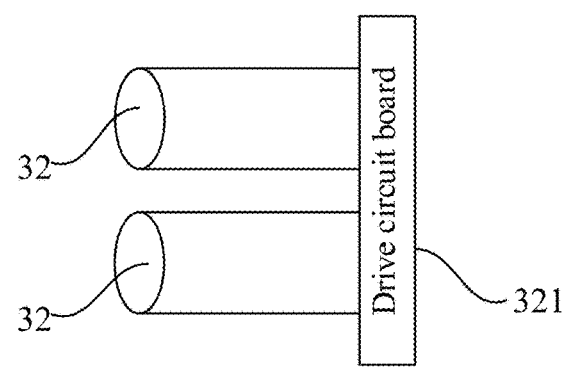
FIG. 8 is a structural schematic diagram of a camera unit in a dental endoscope provided by an embodiment of the present application.
Figure 9:
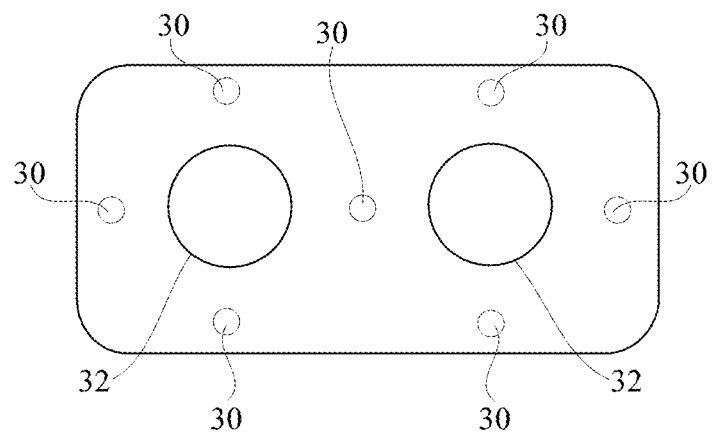
FIG. 9 is a structural schematic diagram of a camera unit in a dental endoscope provided by another embodiment of the present application.

In a first embodiment, as shown in FIG. 8 and FIG. 9, each camera unit 31 includes two cameras 32 with their relative positions being calibrated, that is, relative positions of two cameras 32 are calibrated as internal parameters of the camera unit 31, and the two cameras are also called binocular camera. Specifically, the two cameras 32 can be installed on a same drive circuit board 321, and image capturing areas are overlapped and exposed synchronously, thus depth information of a subject can be acquired through the two cameras 32. In addition, true color (RGB) information of the subject can also be acquired through the two cameras 32, therefore, the camera unit 31 can acquire three-dimensional true color information (RGBD) of the subject.

Figure 10:
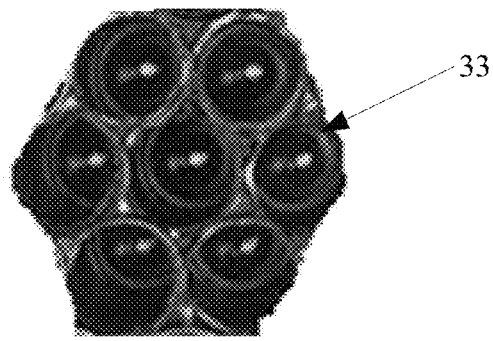
FIG. 10 is a structural schematic diagram of a camera unit in a dental endoscope provided by another embodiment of the present application.

In a second embodiment, as shown in FIG. 10, each camera unit 31 includes a camera array 33 composed of a plurality of cameras with calibrated relative positions, that is, relative positions of the plurality of cameras are calibrated as internal parameters of a camera unit 31, and the multiple cameras are also called multi-view camera. Specifically, image capturing areas of the plurality of cameras are overlapped and exposed synchronously, thus depth information of a subject can be acquired through the plurality of cameras. In addition, true color (RGB) information of the subject can also be acquired through the plurality of cameras, therefore, the camera unit 31 can acquire three-dimensional true color information (RGBD) of the subject. Preferably, the above camera array 33 can include seven cameras.

Figure 11:
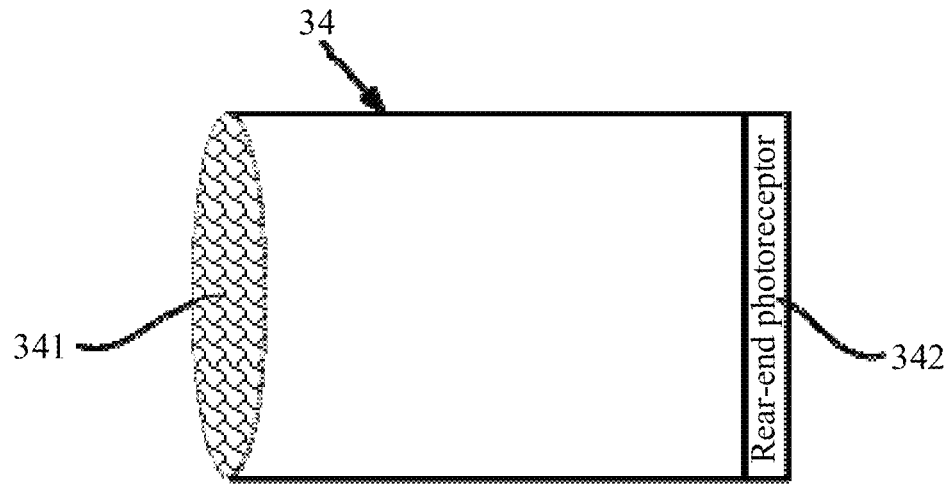
FIG. 11 is a structural schematic diagram of a camera unit in a dental endoscope provided by another embodiment of the present application.

In a third embodiment, each camera unit 31 includes one light field camera; specifically:

In a first manner, as shown in FIG. 11, a light field camera 34 can include a front-end master lens 341 and a rear-end photoreceptor 342, where the front-end master lens 341 is a microlens array composed of multiple microlenses (specifically a camera array in FIG. 10 can be adopted), each microlens can perform focusing and imaging for images respectively on the rear-end photoreceptor 342 (for example, a CMOS photosensitive chip) from different angles, so as to acquire depth information of a subject; preferably, the front-end master lens 341 of the light field camera 34 can be composed of seven microlenses.

Figure 12:
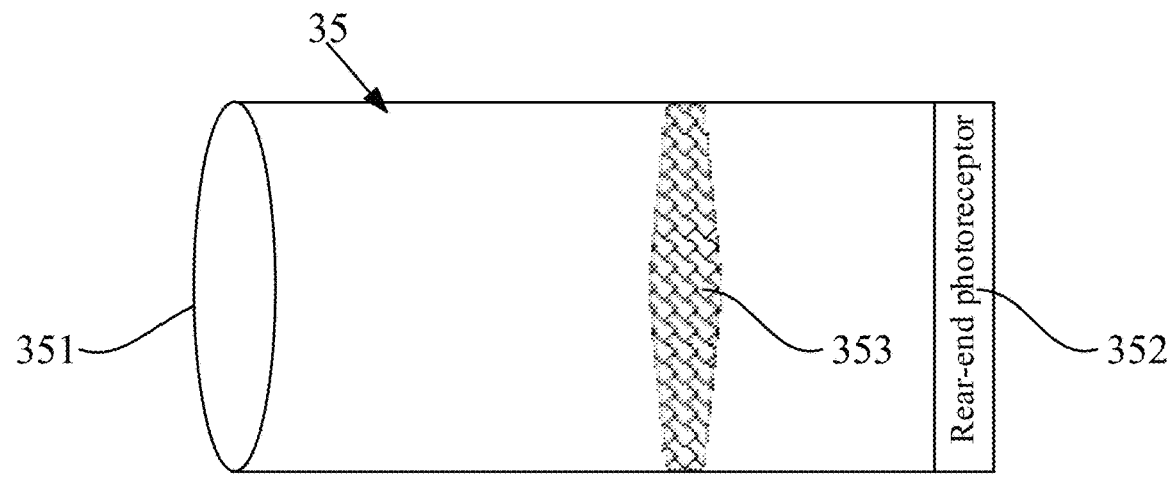
FIG. 12 is a structural schematic diagram of a camera unit in a dental endoscope provided by another embodiment of the present application.
Figure 13:
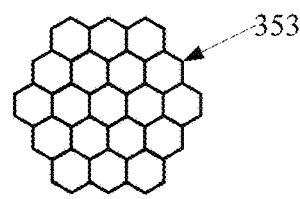
FIG. 13 is a structural schematic diagram of a microlens array in a camera unit as shown in FIG. 12.

In a second manner, as shown in FIG. 12 and FIG. 13, a light field camera 35 can include a front-end master lens 351 and a rear-end photoreceptor 352, and a microlens array 353 arranged between the front-end master lens 351 and the rear-end photoreceptor 352; where one lens constitutes the front-end master lens 351; the microlens array 353 is composed of multiple microlenses, and each microlens can perform focusing and imaging for images respectively on the rear-end photoreceptor (for example, a CMOS photosensitive chip) from different angles, so as to acquire depth information of a subject; preferably, the microlens array 353 can be composed of 19 microlenses.

Specifically, the above two light field cameras can also acquire true color (RGB) information of a subject, so that the camera unit 31 provided in the present embodiment can acquire three-dimensional true color information (RGBD) of a subject.

As shown in FIG. 1 to FIG. 6, on the basis of the above embodiments, in one specific embodiment, in the image acquisition module 3, illumination units are in one-to-one correspondence with camera units 31, and each illumination unit is arranged on the periphery of its corresponding camera unit 31, to provide illumination to its corresponding camera unit 31.

Optionally, each illumination unit and its corresponding camera unit 31 can be matched; for example, a power-supply line of each illumination unit, and a power-supply line of a camera unit 31 corresponding to each illumination unit can be shared with each other.

Preferably, each illumination unit can include at least one light-emitting diode (LED); of course, a miniature laser transmitter can also be adopted for illumination.

Specifically, as to layout of illumination units, there are the specific embodiments as follows.

In a first manner, as shown in FIG. 9, when the camera unit 31 is a binocular camera, seven micro LED lights 30 are used to provide illumination to calibrated binocular cameras which are exposed synchronously; specifically, one LED light 30 is arranged between two cameras of the binocular camera, and the other six LED lights 30 are arranged to surround the two cameras uniformly, and thus each camera is surrounded by four LED lights 30.

In a second manner, when the camera unit 31 is a multi-view camera or a light field camera, multiple LED lights which surround the camera uniformly can be adopted to provide illumination to the camera unit 31.

In a third manner, a miniature laser transmitter (a laser diode) is arranged on the periphery of each camera unit 31, illumination can be provided by the laser diode and interference from other visible lights can be prevented, so as to realize image capturing at a higher quality; meanwhile, the camera unit 31 can also be supported to perform phase three-dimensional laser scanning on the inside of an oral cavity.

As shown in FIG. 1 to FIG. 6, on the basis of the above embodiments, in one specific embodiment, the image acquisition module 3 can further include surface structured light projection units which are in one-to-one correspondence with the camera units 31, and the surface structured light projection unit is arranged on the periphery of its corresponding camera unit 31 and is configured to provide structured light to its corresponding camera unit 31.

Specifically, an illumination unit can provide white-light illumination to its corresponding camera unit 31, to support the camera unit 31 to acquire true color (RGB) image of an internal surface of an oral cavity; a surface structured light projection unit can provide structured light to its corresponding camera unit 31, so as to realize structured light coding measurement on an internal surface of an oral cavity, and further to acquire depth information of a subject, such that three-dimensional reconstruction of an oral endoscopic image is more accurate and rapid; therefore, the image unit 31 can acquire true color three-dimensional image of an internal surface of an oral cavity through the match between the surface structured light projection unit and the camera unit.

Preferably, the illumination unit and a surface structured light projection unit corresponding to each camera unit 31 can be rapidly and alternately turned on and off under the control of the master control module 42, to facilitate the camera unit 31 to acquire in sequence true color (RGB) information and depth information of a subject.

Optionally, in order to rapidly and accurately acquire an RGBD three-dimensional true color image, the illumination unit, the surface structured light projection unit and the camera unit 31 can be implemented as in the following three specific embodiments.

In a first manner, a visible light source is used as an illumination unit, and an infrared source is used as a surface structured light projection unit. Each camera unit 31 includes two cameras, relative positions of which are calibrated as internal parameters of a camera unit 31. One of the cameras is an infrared camera and is used in conjunction with the surface structured light projection unit to capture depth images with surface structured light projections, and the other camera is a visible light camera, and is used in conjunction with an illumination light source to capture RGB images; specifically, the surface structured light source and the illumination unit can be turned on and off successively, so as to finish acquisition of depth images and RGB images successively.

In a second manner, an illumination light source and a surface structured light projection unit are integrated into one light source device, specifically, the light source device includes a visible light source and a projection structure, the projection structure can be switched before a light outlet surface of the visible light source, such that two functions of the light source device, surface structured light projection and visible light illumination, can be switched from one to another; at this time, the camera unit 31 can only be provided with one camera, and depth images with surface structured projections and RGB images without surface structured projections are captured in turn successively through the camera 31.

In a third manner, on the basis of a light source device mentioned in the second manner, each camera unit 31 can also be provided with two cameras whose relative positions are calibrated as internal parameters of the camera unit 31, and the two cameras are respectively configured to capture depth images with surface structured projections and RGB images without surface structured projections.

On the basis of each of the above embodiments, as to the setting of the housing, there are two specific embodiments as follows.

Figure 16:
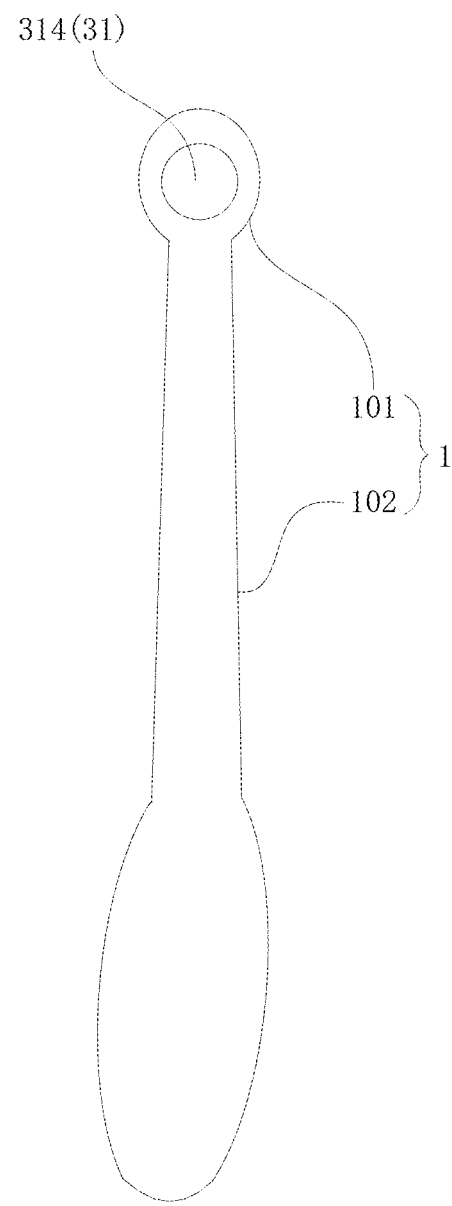
FIG. 16 is a structural schematic diagram of a dental endoscope provided by another embodiment of the present application.
Figure 17:
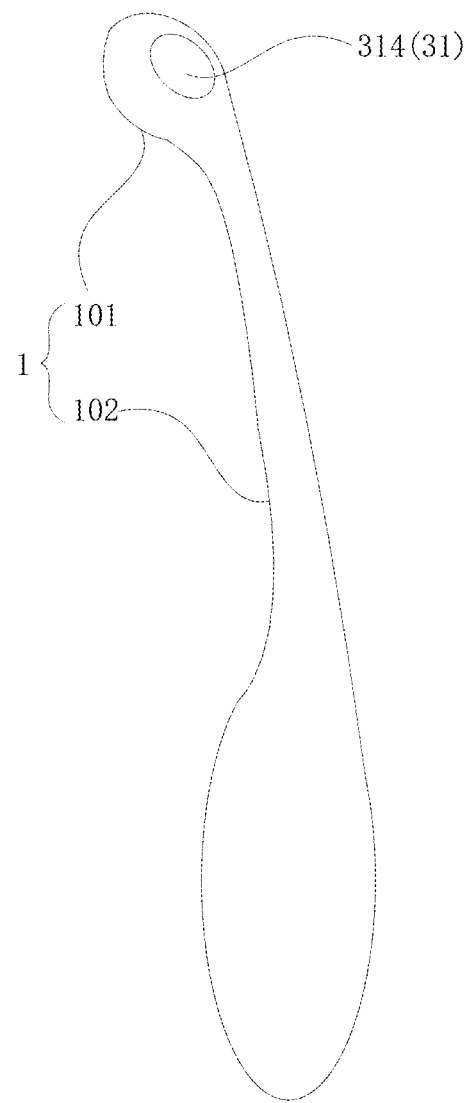
FIG. 17 is a structural schematic diagram of a dental endoscope of FIG. 16 under another angel of view.

In a fourth embodiment, as shown in FIG. 16 and FIG. 17, the a housing 1 can include a probe part 101 and a handheld part 102; specifically, the handheld part 102 can be various shapes convenient for grasping by hands, for example, the handheld part 102 can be of a rod shape with a diameter being gradually increased from one end close to the probe part 101 to the other end.

Optionally, the probe part 101 and the handheld part 102 are of an integrated structure.

As shown in FIG. 16 and FIG. 17, in one specific embodiment, the image acquisition module is arranged inside the probe part 101; preferably, the probe part 101 is flat; such that, when an image of user's teeth is captured, the probe part 101 can be accommodated and move freely within such a narrow area as an oral vestibule, so as to improve user experience.

As shown in FIG. 16 and FIG. 17, on the basis of the above embodiments, in one specific embodiment, an image acquisition module can include two camera units 314 which are arranged back to back, and two illumination units which respectively provide illumination to the two camera units 314; specifically, two camera units 314 are respectively arranged to face two flat surfaces of a probe part 101, that is, the two camera units 314 respectively acquire images towards opposite directions through two flat surfaces of the probe part 101.

As shown in FIG. 16 and FIG. 17, on the basis of the above embodiments, in one specific embodiment, structures of two camera units 314 are completely identical; further, axes of two camera units 314 are in mutual coincidence.

In a fifth embodiment, as shown in FIG. 1 to FIG. 6, a housing 1 can be ellipsoid-shaped, or cylinder-shaped with end faces 11 at two ends being camber surfaces, or rounded-corner-column-shaped with end faces 11 at two ends being camber surfaces; specifically, the housing 1 can be similar to a capsule in form; such that, when an oral image is acquired, the whole housing 1 can be placed in an oral cavity, and the housing 1 can sufficiently roam in an oral cavity through a tongue, to acquire images of the respective positions of the oral cavity, so that a user is prevented from opening the mouth for a long time during the process of tooth scanning, so as to improve user experience; moreover, the housing 1 of the above shape facilitates roaming in an oral cavity of a user, and especially facilitates accommodation and movement of the housing 1 in such narrow areas as an oral vestibule, so as to improve user experience; of course, in practical applications, the housing 1 is not limited to the above shapes, and can also be of other shapes, mainly standardized by improving user experience.

As shown in FIG. 1 to FIG. 6, in one preferred embodiment, proper material selection and structural design is made to allow the above housing 1 have features applicable to being placed in an oral cavity such as being transparent, tenacious, non-toxic, tasteless, waterproof, corrosion-resistant, skin-friendly and comfortable, for example, the housing 1 can be made of such materials as tempered lens glass and transparent polymer materials.

As shown in FIG. 1 to FIG. 6, on the basis of the above embodiments, in one specific embodiment, the above housing 1 includes two end faces 11 which are set oppositely, and a side face arranged between two end faces 11; specifically, the side face of the housing 1 is divided into two first side faces 12 arranged oppositely and two second side faces 13 arranged oppositely, for example, when the housing 1 is ellipsoid-shaped or cylinder-shaped with end faces 11 at two ends being camber surfaces, the two first side faces 12 and two second side faces 13 of the housing 1 are all rotating surfaces; when the housing 1 is rounded-corner-column-shaped with end faces 11 at two ends being camber surfaces, two first side faces 12 of the housing 1 can be flat surfaces, and two second side faces 13 can be rotating surfaces. At this time, there are several embodiments for the image acquisition module 3 as follows.

In a first manner, an image acquisition module 3 can include two pairs of first camera units 311, and the two pairs of first camera units 311 are respectively arranged at two end parts, along a direction of a long axis o, of a housing 1, that is, an area close to two end faces 11 of the housing 1; further, two first camera units 311 in each pair of first camera units 311 are arranged back to back, and cameras of the two first camera units 313 respectively face two first side faces 12 of the housing 1.

In a second manner, on the basis of manner 1, an image acquisition module 3 can further include two second camera units 312, and the two second camera units 312 are distributed in a cross section a of a housing 1 in which a center of the housing 1 is located, that is, within a middle area of the housing 1; further, the two second camera units 312 are arranged back to back, and cameras of the two second camera units 312 respectively face two second side faces 13 of the housing 1.

In a third manner, on the basis of the first manner or the second manner, the image acquisition module 3 can further include two third camera units 313, and the two third camera units 313 are respectively arranged at two end parts, along a direction of a long axis o, of the housing 1, that is, an area close to two end faces 11 of the housing 1; further, the two third camera units 313 are arranged back to back, and cameras of the two third camera units 313 respectively face two end faces 11 of the housing 1.

It should be noted that, the above first camera unit 311, the second camera unit 312 and the third camera unit 313 are distinguished and named according to their positions and arrangement features, and their specific structures can be completely identical.

Moreover, preferably, a gap between a camera of each of the above camera units 31 (first camera unit 311, second camera unit 312 and third camera unit 313) and the housing 1 can be larger than or equal to the minimum focal length of the camera unit 31, for example, 3 mm to 7 mm, such that a camera of the camera unit 31 can be focused accurately, and further unclear pictures are avoided.

The above several manners for arranging the image acquisition module 3 can ensure that when the housing 1 roams in such regions as an oral vestibule, an occlusal clearance and an oral cavity proper, the image acquisition module 3 can sufficiently acquire images of each side face (a jaw-side face, a tongue-side face and a chewing surface) of each tooth, so as to acquire three-dimensional image information of complete dentition, and further form a digital model of a complete dentition.

In addition, the above several manners for arranging the image acquisition module 3 enable the dental endoscope to acquire three-dimensional images of other structures in an oral cavity, for example, a tongue and an oral mucosa, therefore, a user can also utilize the above dental endoscope to perform self-inspection on oral health.

Figure 7:
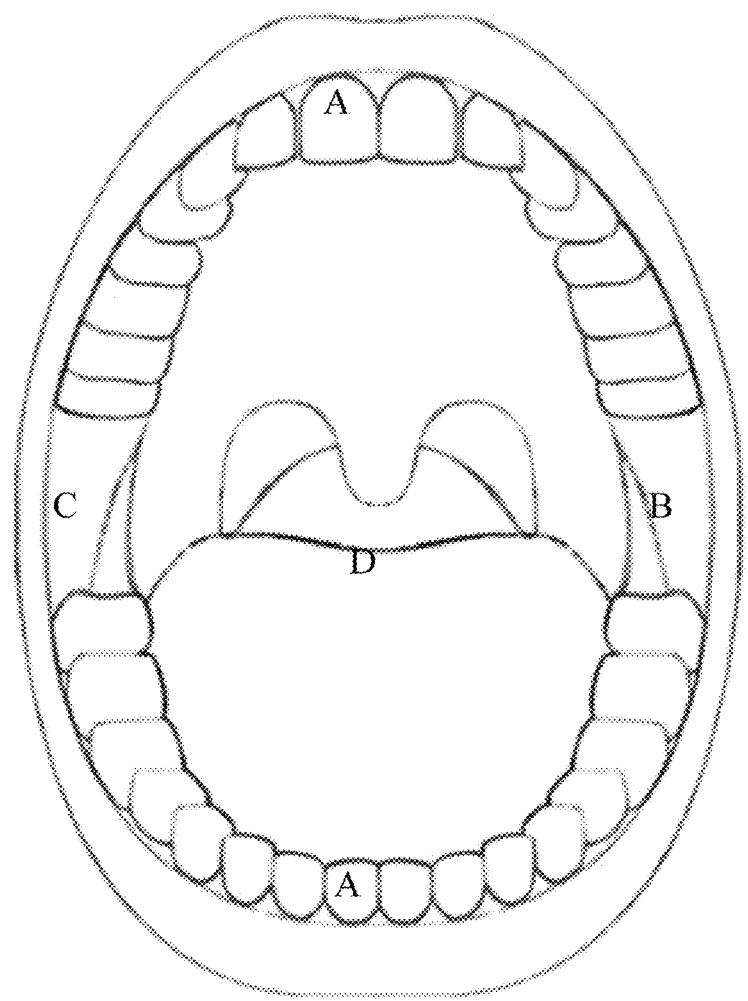
FIG. 7 is a structural schematic diagram of an oral cavity provided by an embodiment of the present application.

As shown in FIG. 7, in one specific embodiment, image acquisition areas of the above dental endoscope can include: an oral vestibule A, a left occlusal clearance B, a right occlusal clearance C and an oral cavity proper D.

Of course, the above several manners for arranging an image acquisition module are merely several specific embodiments of examples of the present application, and an image acquisition module in the dental endoscope in the present application is not limited to the above embodiments.

As shown in FIG. 5 to FIG. 6 and FIG. 14 to FIG. 15, on the basis of the above embodiments, in one specific embodiment, the dental endoscope in the present application can further include a stretching part 2, specifically, the stretching part 2 is arranged outside the housing 1, and one end of the stretching part 2 is connected with the housing 1.

Further, the stretching part 2 can include a connector 21 with one end being connected with the housing 1, and a handle 22 which is connected with the other end of the connector 21.

As shown in FIG. 5 to FIG. 6 and FIG. 14 to FIG. 15, on the basis of the fifth embodiment, in one specific embodiment, the connector 21 in the stretching part 2 can be set in the following two manners.

In a first manner, the connector 21 can be a rigid connecting rod; specifically, on the one hand, the connecting rod can prevent a housing 1 from being swallowed carelessly by a user or from causing asphyxia; on the other hand, a user can grasp a connecting rod with hands, through conduction of a force by the connecting rod, the housing 1 is operated to move in an oral cavity, such that the housing 1 sufficiently roams in the oral cavity.

In a second manner, the connector 21 can also be a soft drawstring, and the drawstring can also prevent a housing 1 from being swallowed carelessly by a user or from causing asphyxia; moreover, when the connector 21 is a drawstring, a user can enable the housing 1 to sufficiently roam in an oral cavity by means of movement of the tongue and teeth.

Figure 14:
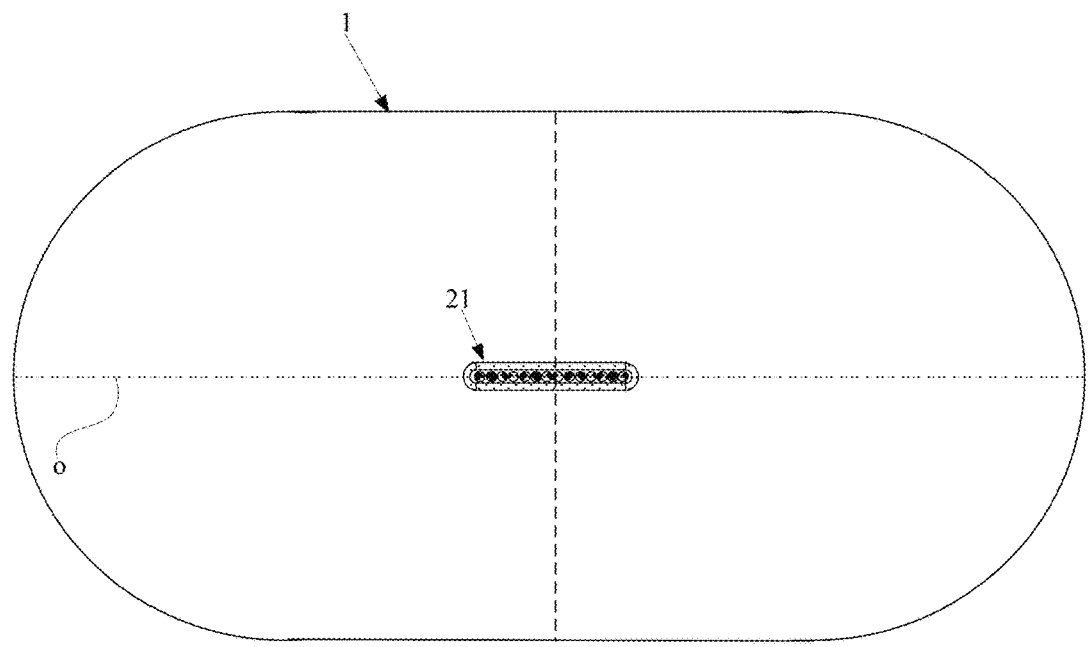
FIG. 14 is a structural schematic diagram of a section at one end, close to a housing, of a connector in a dental endoscope provided by an embodiment of the present application.

As shown in FIG. 14, on the basis of the above embodiments, in one preferred embodiment, the connector 21 is flat, at an end close to a housing 1, an extension direction of a cross section of the connector 21 is in parallel with a direction of a long axis o of the housing 1.

Further preferably, the thickness of the connector 21 is no larger than 1.5 mm.

Based on a shape of the housing 1 and spatial distribution inside an oral cavity of a human body, when the housing 1 is accommodated in an oral cavity, a long axis direction of the housing 1 is often consistent with an arrangement direction of teeth; at this time, since the cross section of the connector 21 is flat along the direction of the long axis of the housing 1, therefore, the connector 21 can extend outwards from an oral cavity only when user's lips are opened slightly.

Figure 5:
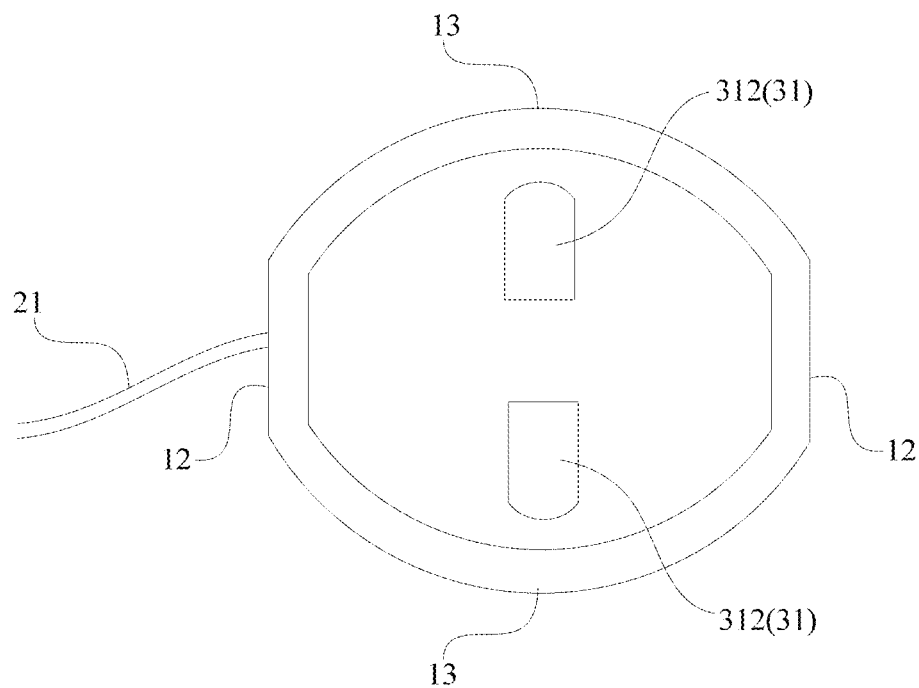
FIG. 5 is a sectional structural schematic diagram of a dental endoscope along a central cross section of a housing of the dental endoscope provided by another embodiment of the present application.
Figure 6:
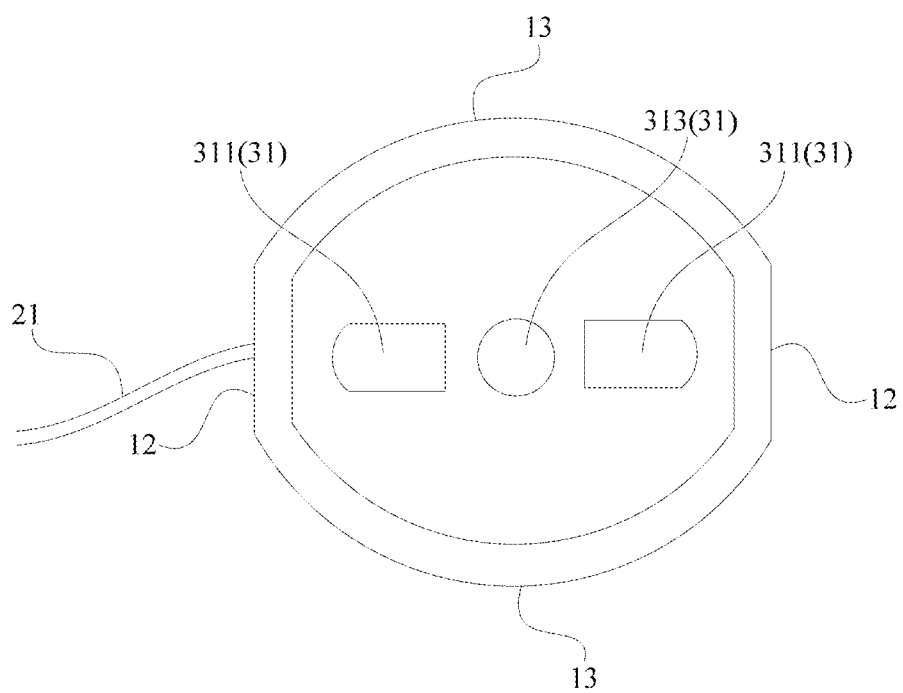
FIG. 6 is a sectional structural schematic diagram of an end part in a long axis of the housing of the a dental endoscope in FIG. 5.

As shown in FIG. 5 and FIG. 6, further preferably, based on a distribution manner of camera units 31 provided in an embodiment of the present application, one end of the connector 21 can be connected to a middle part of the first side face 12 of the housing 1; at this time, the connector 21 will not block any camera unit 31 in the housing 1.

Figure 15:
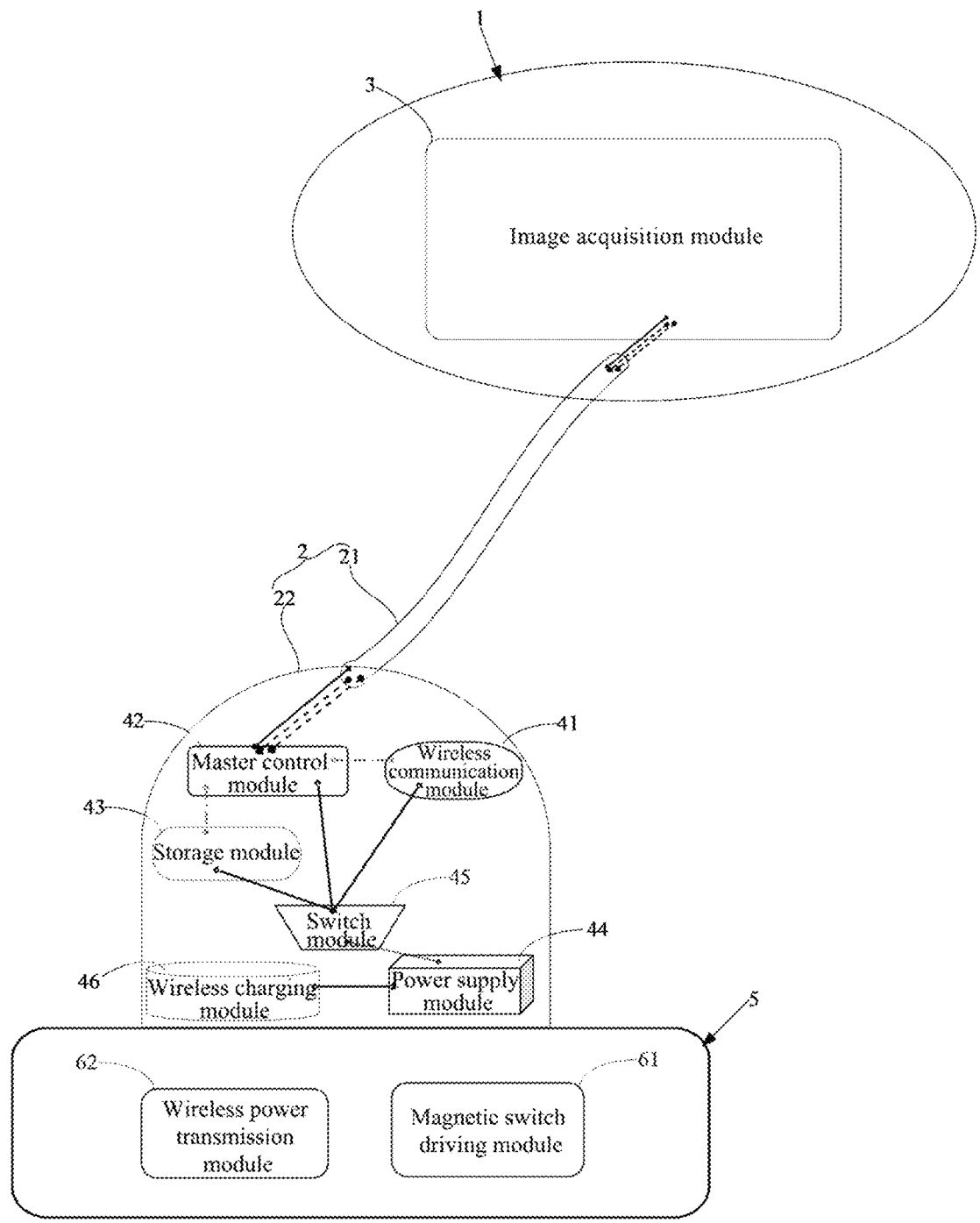
FIG. 15 is a structural schematic diagram of a dental endoscope provided by another embodiment of the present application.

As shown in FIG. 14 and FIG. 15, on the basis of the above embodiments, in one specific embodiment, the connector 21 of the stretching part 2 can include an electrical connecting line which is used for electrical connection between a module in a housing 1 and a module in the handle 22.

As shown in FIG. 15, on the basis of each of the above embodiments, in one specific embodiment, the dental endoscope provided by an embodiment of the present application can further include a master control module 42 and a storage module 43, where the storage module 43 is configured to store images acquired by an image acquisition module 3; the master control module 42 is respectively in signal connection with the image acquisition module 3, the storage module 43 and the wireless communication module 41. Specifically, the master control module 42 can control each camera unit 31 in the image acquisition module 3 to acquire three-dimensional image information, and send acquired three-dimensional image information to the storage module 43 for storage; further, the master control module 42 can further transmit image information stored by the storage module 43 to the wireless communication module 41, such as an electric equipment terminal or a cloud server, so as to process and display images.

Specifically, the master control module 42 can control all the camera units 31 in the image acquisition module 3 to synchronously expose and acquire images.

Since the image acquisition module 3 includes at least two camera units 31, and relative positions of the at least two camera units 31 are calibrated, three-dimensional image information acquired during synchronous exposure and acquisition of the at least two camera units 31 can be taken as a reference mutually, so as to improve efficiencies in image acquisition and three-dimensional modeling.

Further, after the master control module 42 receives image information acquired by an image acquisition module 3, the master control module 42 can at least add corresponding timestamp information of image acquisition and identification of camera units 31 to the image information, and send image information after adding to the storage module 43 for storage.

In this way, image information is added with corresponding timestamp information of image acquisition and identification of camera units 31, for example, in an embodiment of the present application, each camera unit 31 can be set with a number, and the number is taken as a unique identification of each camera unit 31.

Therefore, a receiving end of image information can clearly know time of image acquisition of each piece of image information, image information acquired when camera units 31 are exposed simultaneously will have identical timestamp information, and that the image information is acquired by which camera unit 31 can also be known, further the master control module 42 sends to an external device image information which is added with timestamp information and identification of the camera unit 31 through the wireless communication module 41, so as to provide more valid information to an external device. For example, an external device can respectively synthesize images acquired at synchronously according to timestamp information, thereby facilitating the external device to determine specific position information of each piece of image information in an oral cavity according to the information, and facilitating three-dimensional image synthesis and splicing processing on different image information.

As shown in FIG. 15 to FIG. 17, on the basis of the above embodiments, in one specific embodiment, on the basis of the fifth embodiment 5, the master control module 42 and the storage module 43 can both be arranged in the handle 22 of the stretching part 2, and can be in signal connection with the image acquisition module 3 through an electrical connecting line in the connector 21; further, the wireless communication module 41 is also arranged in the a handle 22; in another specific embodiment, on the basis of the fourth embodiment, the master control module 42, the storage module 43 and the wireless communication module 41 can all be arranged in the a handheld part 102 of the housing 1.

In one preferred embodiment, the image acquisition module 3 can also be in signal connection with the storage module 43 through a master control module 42; moreover, according to requirements of image information processing, the master control module 42 can include a Digital Signal Processor (DSP) processing unit, further, after the camera unit 31 transmits original pixel digital information to the master control module 42, the DSP processing unit in the master control module 42 can perform optimization processing on the original pixel digital information sent by the camera unit 31, generate image coded data, and store the data in the storage module 43.

Optionally, the image acquisition module 3 can be charged with electricity through the master control module 42; specifically, the image acquisition module 3 and the master control module 42 can be connected through a data line and a Universal Serial Bus (USB) interface, for example, the data line can include two power lines configured to supply power to the camera unit 31, and two serial communication buses configured to transmit control signals and digital image information; specifically, the image acquisition module 3 can receive control instructions, such as starting of image capture, stopping of image capture, setting of focal length, and frames per second, sent by the master control module 42 through a data line; moreover, the image acquisition module 3 can also send back captured digital image information through the data line.

Further, according to requirements of image information processing, the master control module 42 can further include a three-dimensional image information preprocessing unit, to finish a preprocessing task of three-dimensional image information, for example, for the condition that the camera unit 31 is a binocular camera, during preprocessing of three-dimensional image information, a binocular computer vision algorithm (this is a commonly used technique in the field, and the output format of the algorithm is RGBD) can be adopted to perform preprocessing of three-dimensional image information. Specifically, functions of a three-dimensional image information preprocessing unit can be specifically realized by adopting FPGA.

It should be noted that, the above DSP processing unit can also be integrated in the camera unit 31, that is, the camera unit 31 directly transmits image coding data (for example, JPEG format) after optimization processing to the master control module 42; in addition, the master control module 42 can also be provided with no three-dimensional image information preprocessing unit, that is, the master control module 42 directly sends image coding data (for example, JPEG format) to other devices (for example, an electric equipment terminal or a cloud server), and then images can be processed through a three-dimensional image information preprocessing unit in other devices.

As shown in FIG. 15, on the basis of the above embodiments, in one specific embodiment, the dental endoscope provided by an embodiment of the present application can further include a power supply module 44, which is configured to supply power to each power module in a dental endoscope.

As shown in FIG. 15, on the basis of the above embodiments, in one specific embodiment, the dental endoscope provided by an embodiment of the present application can further include a switch module 45, specifically, the switch module 45 is arranged between the a power supply module 44 and each electric module, and is configured to control on and off states of a circuit by which the power supply module 44 provides power to each electric module.

As shown in FIG. 15 to FIG. 17, on the basis of the above embodiments, in one specific embodiment, on the basis of the fifth embodiment, the power supply module 44 and the switch module 45 can both be arranged in the handle 22 of the stretching part 2; in another specific embodiment, on the basis of the fourth embodiment, the power supply module 44 and the switch module 45 can both be arranged in the handheld part 102 of the housing 1.

Specifically, the power supply module 44 can be directly in electrical connection with the a master control module 42, the storage module 43 (containing an First Input First Output (FIFO) storage unit, and further containing other memory contents, such as ID of intelligent hardware, etc.) and the a wireless communication module 41, so as to provide power to each of the above electric modules; in addition, the power supply module 44 can supply power to the image acquisition module 3 through the master control module 42; of course, the power supply module 44 can also directly supply power to the image acquisition module 3 in a housing 1 through an electrical connecting line in the connector 21.

As shown in FIG. 15, on the basis of the above embodiments, in one specific embodiment, the above switch module 45 can adopt a magnetic switch unit to control on and off states of a power supply circuit; correspondingly, the dental endoscope provided by an embodiment of the present application can further include a magnetic switch driving module 61 which is configured to drive a magnetic switch unit to perform turning on and off actions.

As shown in FIG. 15, on the basis of the above embodiments, in one specific embodiment, the dental endoscope provided by an embodiment of the present application can further include a base 5, where the base 5 is arranged to be independent of the housing 1; further, the magnetic switch driving module 61 can be arranged inside the base 5. At this time, positions of the magnetic switch driving module 61 and a magnetic switch unit can be matched or mismatched by controlling the relative positions between the housing 1 and/or the stretching part 2, and the base 5, to control the switch module 45 on or off.

Preferably, the power supply module 44 can include a power supply adaptive unit, which is configured to supply power to each electric module in a matching manner.

As shown in FIG. 15, on the basis of the above embodiments, in one specific embodiment, the dental endoscope provided by an embodiment of the present application can further include a wireless charging module 46, and the wireless charging module 46 is configured to acquire external power and provide power to the power supply module 44; correspondingly, the dental endoscope provided by an embodiment of the present application can further include a wireless power transmission module 62 in match with the wireless charging module 46; specifically, the wireless charging module 46 can be charged by receiving current emitted by the wireless power transmission module 62.

As shown in FIG. 15 to FIG. 17, in a preferred embodiment, on the basis of the fifth embodiment, the wireless charging module 46 is arranged in the handle 22; and the wireless power transmission module 62 is arranged in the base 5. At this time, position matching between a wireless power transmission module 62 and the wireless charging module 46 can be realized through placing the handle 22 on the base 5, and further the wireless charging module 46 can be charged; otherwise, when the handle 22 is taken away from the base 5, the charging of the wireless charging module 46 is stopped. In another preferred embodiment, on the basis of the fourth embodiment, the wireless charging module 46 is arranged in the handheld part 102 of a housing 1; and the wireless power transmission module 62 is arranged in the base 5; similarly, at this time, the handheld part 101 of the housing 1 can be placed on or taken away from the base 5, so as to realize charging or stop charging.

Of course, a directly-charging power module can be further arranged in the handle 22 or the handheld part 102 of the housing 1, specifically, a power plug can be arranged in the handle 22 or the handheld part 102 of the housing 1, so as to directly charge the directly-charging power module.

It should be noted that, in the above dental endoscope, on the basis of the fifth embodiment, the respective modules except the magnetic switch driving module 61 and the wireless power transmission module 62 can also be integrated in the housing 1, at this time, the connector can be a common cord which does not include an electrical connecting line.

As to the dental endoscope of an embodiment of the present application, tooth cleaning situation can be displayed in a situational manner through an electric equipment terminal, so as to encourage an interest in teeth brushing and encourage a user to form a good teeth cleaning habit, therefore, the dental endoscope is very applicable to children who are unwilling to brush teeth; moreover, teeth modeling can be performed by the dental endoscope to substitute plaster teeth modeling and traditional optical teeth modeling, thereby facilitating persons who need to take teeth impression; in addition, the dental endoscope can facilitate a user in self-endoscopy of images of a complete dentition, thereby facilitating persons who care health and cleanliness of teeth to know in real time health and cleanliness of teeth and gingiva.

An embodiment of the present application further provides a dental endoscopic device, and the dental endoscopic device includes the dental endoscope in any of the above embodiments.

In one specific embodiment, the above dental endoscopic device can further include an electric equipment terminal which is in data connection with the dental endoscope; optionally, the electric equipment terminal can include an internet networking module, a wireless communication module, a CPU and storage module, a display module and a man-machine operation interface, to facilitate synthesis and display of a three-dimensional image; further, the electric equipment terminal can be provided with corresponding dental endoscopic application software.

Specifically, the electric equipment terminal can be a smart phone, a PAD, a notebook computer or a desktop computer of a user, or a computer terminal device specially used for dental endoscopy.

Based on each of the above embodiments in embodiments of the present application, the dental endoscope sends a captured image to an external device, for example, an electric equipment terminal or a cloud server, to perform three-dimensional image synthesis, and a procedure of each method during specific applications of the dental endoscope is described in detail below only with an image which is sent to an electric equipment terminal for three-dimensional image synthesis as an example.

Figure 18:
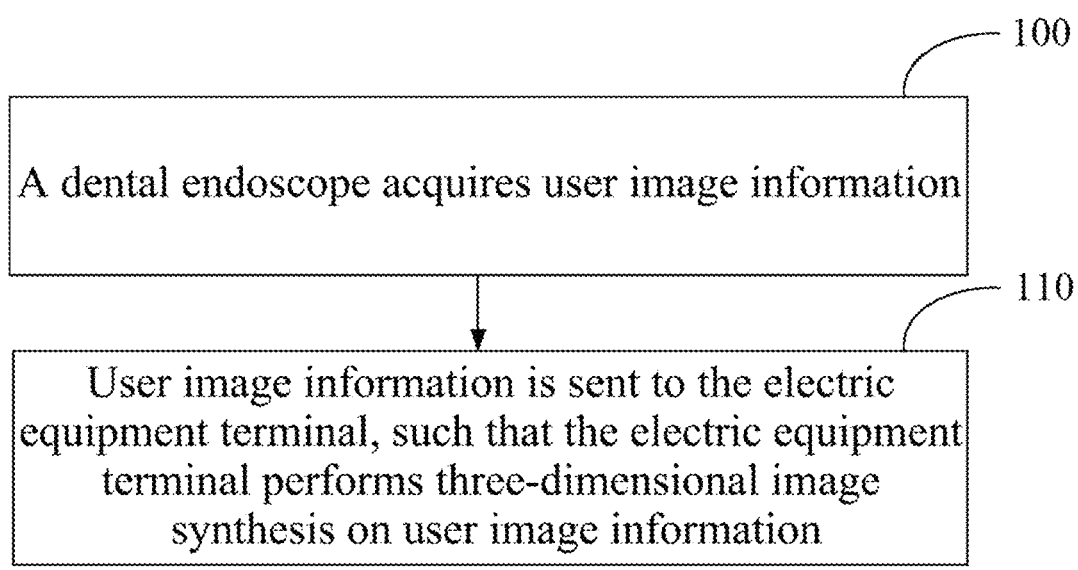
FIG. 18 is an operating flow chart of a dental endoscope provided by an embodiment of the present application.

Taking a dental endoscope structure shown in FIG. 15 as an example, and referring to FIG. 18, in an embodiment of the present application, an operating flow of the dental endoscope includes:

Step 100: a dental endoscope acquires user image information.

Specifically, since the image acquisition module 3 at least includes two camera units 31, acquired user image information at least includes image information captured by two camera units 31.

Moreover, each camera unit 31 can acquire three-dimensional image information, and the type of acquired user image is depth image.

In one specific embodiment, the base 5 can also be provided with the control processing module and the wireless communication module, where the control processing module is configured to exchange information with the master control module 42 in the handle 22 through the wireless communication module, to realize information interaction and data communication.

Further, before step 100 is performed, an operating procedure of starting the dental endoscope is further included, specifically, after the dental endoscope is started, the following operations can further be performed.

The first operation: the master control module 42 in the handle 22 sends a first handshake message to the base 5 according to a first preset period, and receives a response message of the first handshake message returned by the base 57.

Specifically, the master control module 42 can start a timer (a handle 22-base 5 handshake timer), the master control module 42 invokes a wireless communication module 41 to send the first handshake message to the base 5 according to the first preset period, for example, 5 seconds or 10 seconds.

Here, the first preset period is not limited in an embodiment of the present application, and its value can be set according to actual requirements.

In this way, the base 5 can monitor whether the dental endoscope is in a normal state, and further prompt or alarm the user.

The second operation: the master control module 42 in the handle 22 sends a handshake message to an electric equipment terminal according to a preset period, and determines within a first preset time duration that a response message of handshake message returned by an electric equipment terminal is received, where the handshake message at least includes device identification of a dental endoscope.

Here the preset period is not limited in an embodiment of the present application, and can be set according to actual requirements.

Specifically, the master control module 42 can start a timer (dental endoscope-terminal handshake timer), the master control module 42 invokes the wireless communication module 41 to send a handshake message to the electric equipment terminal according to the preset period, for example, 2 seconds or 5 seconds, if the master control module 42 receives a response message of handshake message returned by the electric equipment terminal within a first preset time duration, for example, 30 seconds or 60 seconds, then it indicates that the dental endoscope and the electric equipment terminal have succeeded in handshaking, and communication can be performed, then the dental endoscope performs image acquisition operation again, so as to improve working efficiency of the dental endoscope.

Further, if a response message of handshake message returned by the electric equipment terminal is not received within a first preset time duration, then a signal prompting that endoscopic software of the electric equipment terminal should be opened is sent to the base 5, such that the base 5 sends to a user the prompt information according to the signal prompting that endoscopic software of the electric equipment terminal should be opened.

That is to say, after the dental endoscope is started, the master control module 42 in the handle 22 sends a handshake message to the electric equipment terminal, if a returned response message of handshake message is not received within a first preset time duration, it indicates that handshake between the dental endoscope and the electric equipment terminal is not successful, then the master control module 42 of the dental endoscope sends to the base 5 a signal, prompting that endoscopic software of the electric equipment terminal should be opened, through the wireless communication module 41, after the base 5 receives the signal prompting that endoscopic software of the electric equipment terminal should be opened, the base 5 can send speech prompt information to a user, for example, the prompt content is as follows: an endoscopic application software on the electric equipment terminal cannot be connected, and please open the software and keep the wireless connection on.

Further, after the above second operation is performed, that is, handshake between the dental endoscope and the electric equipment terminal is successful, before performing step 100, the following steps are further included.

A user authentication passed message, sent by the electric equipment terminal is received, where the user authentication passed message is sent when the electric equipment terminal determines that user authentication passed according to device identification of the dental endoscope in the handshake message and a mapping relationship between device identification and user identity.

That is to say, after successful handshake between the dental endoscope and the electric equipment terminal, the electric equipment terminal further needs to verify user identity, thereby further improving use experience of users, and enabling that one dental endoscope can only be used by a user passed user authentication.

Here, the user identity can be a password corresponding to a user or user's biological features, for example, sound, fingerprint, face, etc.

For example, the electric equipment terminal prompts a current user to read a paragraph of text or follow a paragraph of speech, or invokes a camera of the electric equipment terminal to capture a user's face, and compares acquired identity information of a current user with user identity information corresponding to device identification of the dental endoscope to perform authentication by judging whether the two are consistent.

For another example, the electric equipment terminal prompts a current user to input a digital password or a lattice pattern password, compares the received password with a password preset by a user corresponding to a device identification of the dental endoscope, to perform authentication by judging whether the two passwords are consistent.

Further, if user authentication fails, then the electric equipment terminal sends to a user speech or text prompts, for example, the prompt content is as follows: the dental endoscope belongs to other users, please use your own dental endoscope, and you can contact customer service for consultation and help.

Step 110: user image information is sent to the electric equipment terminal, such that the electric equipment terminal performs three-dimensional image synthesis on user image information.

In an embodiment of the present application, the dental endoscope acquires user image information, and the electric equipment terminal performs three-dimensional image synthesis, since the dental endoscope is configured to acquire image information of the oral cavity of a user, if a user takes the dental endoscope out of the oral cavity or does not place the dental endoscope in the oral cavity, then image information acquired by the dental endoscope is no longer image information of the oral cavity, therefore, in order to ensure accurate and effective three-dimensional image synthesis of image information of an oral cavity, whether the dental endoscope is placed in an oral cavity should be further judged, then after performing step 110, the following steps are further included.

If a message confirming that the dental endoscope has been placed in the oral cavity sent by the electric equipment terminal is not received within a second preset time duration, then a prompt that the handle 22 of the dental endoscope should be placed into the base 5 is started, with a reason code as follows: the dental endoscope is not placed in an oral cavity all the time for scanning operation.

Here, the prompt that the handle 22 should be placed into the base 5 is started, specifically as:

the master control module 42 respectively sends a signal prompting that the handle 22 should be placed back to the base 5 to the electric equipment terminal and the base 5, such that the electric equipment terminal and the base 5 respectively send a first prompt information to a user according to the signal prompting that the handle 22 should be placed back to the base 5; where the message confirming that the dental endoscope has been placed in an oral cavity is obtained through judgment by the electric equipment terminal according to received user images and preset image model recognition algorithm.

For example, the first prompt information is as follows: the dental endoscope is not placed in an oral cavity all the time for scanning operation, please place the handle 22 back to the base 5.

Specifically, after the master control module 42 of the dental endoscope sends image information stored in the storage module 43 to the electric equipment terminal through the wireless communication module 41, the electric equipment terminal performs image model recognition, and judges whether the image information is oral image information, if so, the dental endoscope is judged to have been placed in an oral cavity, and a message confirming that the dental endoscope has been placed in an oral cavity is sent to the master control module 42 of the dental endoscope, otherwise, a message confirming that the dental endoscope has been placed in an oral cavity is not sent.

In this way, in an embodiment of the present application, whether the dental endoscope has been placed in an oral cavity is judged, if the dental endoscope is placed in an oral cavity, then the electric equipment terminal or the cloud continues to perform three-dimensional image synthesis, and if the dental endoscope is not placed in an oral cavity all the time, then a user is prompted to place the handle 22 back to the base 5, and no image is captured, thus invalid image capture of the dental endoscope is reduced.

Further, in a process in which the electric equipment terminal performs three-dimensional image synthesis on user image information, the following operations are included.

1) When an image capturing task is finished:

Firstly, if the master control module 42 of the dental endoscope receives a message indicating that an image capturing task has been finished sent by the electric equipment terminal, then the master control module 42 sends a signal indicating that an image capturing task has been finished to the base 5, such that the base 5 sends a third prompt information to a user according to the signal indicating that an image capturing task has been finished; where the message indicating that an image capturing task has been finished is sent after the electric equipment terminal determines that three-dimensional image synthesis has been finished.

Specifically, the master control module 42 sends a signal indicating that an image capturing task has been finished to the base 5 through the wireless communication module 41, and after the base 5 receives the signal indicating that an image capturing task has been finished, the base 5 sends a third prompt information to a user, for example, a speech prompt information, and the content of the third prompt information is as follows: you have succeeded in finishing an oral endoscopic image capturing task.

Afterwards, the master control module 42 respectively sends a signal prompting that the handle 22 should be placed back to the base 5 to the electric equipment terminal and the base 5, such that the base 5 and the electric equipment terminal respectively send a second prompt information to a user according to the signal prompting that the handle 22 should be placed back to the base 5.

For example, the second prompt information is as follows: an image capturing task has been finished, please place the handle 22 back to the base 5.

2) when communication connection is abnormal:

The first condition: the electric equipment terminal sends a communication connection message to the dental endoscope according to a second preset period, if a communication connection response message returned by the dental endoscope is not received within a third preset time duration, then a user is prompted that communication is abnormal.

For example, the electric equipment terminal broadcasts a paragraph of speech prompt or displays a paragraph of prompt information on a screen, and the prompt content is as follows: the communication between the dental endoscope and the oral endoscopic application software is abnormal, please check the communication connection of the dental endoscope.

The second condition: if the master control module 42 of the dental endoscope does not receive communication connection message sent by the electric equipment terminal within a fourth preset time duration, then the master control module 42 sends to the base 5 a signal prompting that the endoscopic software of the electric equipment terminal should be opened, such that the base 5 sends fourth prompt information to a user according to the signal prompting that the endoscopic software of the electric equipment terminal should be opened.

For example, the content of the fourth prompt information is as follows: the endoscopic application software on the electric equipment terminal cannot be connected, please open the software and keep the wireless connection on.

Afterwards, the dental endoscope simultaneously continues to send handshake message to the electric equipment terminal, and judges whether a response message of handshake message returned by the electric equipment terminal has been received.

Further, the following step is also included: if the master control module 42 determines that signals prompting that an endoscopic software of the electric equipment terminal should be opened have been continuously sent to the base 5 for a set number, then a signal prompting that the handle 22 should be placed back to the base 5 is sent to the base 5, such that the base 5 sends to a user the fifth prompt information according to the signal prompting that the handle 22 should be placed back to the base 5.

For example, the number is set to 5 times, the master control module 42 sends to the base 5 a signal prompting that the endoscopic software of the electric equipment terminal should be opened for 5 times successively, which indicates that an endoscopic software of the electric equipment terminal is not open all the time, communication between the dental endoscope and the electric equipment terminal is abnormal, then a prompt that the handle 22 should be placed back to the base 5 is started, with a reason code as follows: the endoscopic application software of the electric equipment terminal is not started for a long time.

After the base 5 receives the signal prompting that the handle 22 should be placed back to the base 5, for example, the base 5 sends the fifth prompt information in speech, and the content of the fifth prompt information is as follows: the endoscopic application software of the electric equipment terminal is not started for a long time, please place the handle 22 back to the base 5.

3) whether the dental endoscope is taken out from an oral cavity is judged:

The first condition: the electric equipment terminal judges whether the dental endoscope has been taken out from an oral cavity according to received user image and a preset image model recognition algorithm, if so, the electric equipment terminal sends to the dental endoscope a message indicating that the dental endoscope has been taken out from an oral cavity, and stops three-dimensional image synthesis; if not, the electric equipment terminal continues to perform three-dimensional image synthesis.

The second condition: if the dental endoscope receives a message indicating that the dental endoscope has been taken out from an oral cavity sent by the electric equipment terminal, then the dental endoscope starts timing of judging whether a message confirming that the dental endoscope has been placed in an oral cavity is received, to continues to judge whether a message confirming that the dental endoscope has been placed in an oral cavity sent by the electric equipment terminal is received within a second preset time duration.

In an embodiment of the present application, in a process of three-dimensional image synthesis, the electric equipment terminal periodically, for example, every 1 second or 2 seconds, judges whether the dental endoscope has been taken out from an oral cavity, if the dental endoscope has been taken out, then the electric equipment terminal can stop three-dimensional image synthesis, to improve accuracy of three-dimensional image synthesis.

It should be noted that, the present endoscopic process is not finished when the dental endoscope is taken out from an oral cavity, and is finished when the dental endoscope is placed back to the base 5, when the dental endoscope is taken out from the base 5, a new endoscopic process is started again, and the process is performed from starting of the dental endoscope.

Further, after the dental endoscope is completely shut down, a charging operation can be performed, specifically as follows.

The dental endoscope receives a wireless power sent by the base 5, acquires and stores power according to the received wireless power, and sends to the base 5 a signal prompting to stop charging when power in the dental endoscope is detected to reach a preset maximum power capacity, such that the base 5 stops sending wireless power to the dental endoscope according to the signal prompting to stop charging.

Evidently those skilled in the art can make various modifications and variations to the embodiments of the present application without departing from the spirit and scope of the present application. Accordingly, the present application is also intended to encompass these modifications and variations thereto so long as the modifications and variations come into the scope of the claims appended to the present application and their equivalents.

The invention claimed is:

1. A dental endoscope, comprising:
   a housing;
   an image acquisition module fixedly installed in the housing and configured to acquire an external image through the housing, wherein the image acquisition module comprises at least two camera units, relative positions of the at least two camera units are calibrated, the at least two camera units are configured to acquire three-dimensional image information, the image acquisition module comprises an illumination unit configured to provide illumination to each camera unit, and at least one pair of the at least two camera units includes cameras units arranged back to back;
a wireless communication module configured to perform wireless communication with an external device and send image information acquired by the image acquisition module to the external device;
a storage module configured to store image information acquired by the image acquisition module; and
a master control module in signal connection with the image acquisition module, the storage module and the wireless communication module, and configured to control each camera unit to synchronously expose and synchronously acquire three-dimensional image information, send acquired three-dimensional image information to the storage module, and transmit image information stored in the storage module to the wireless communication module;
wherein each camera unit comprises a light field camera, and each light field camera comprises a front-end master lens and a rear-end photoreceptor; and
wherein each front-end master lens comprises a microlens array including multiple microlenses, or each light field camera comprises a microlens array arranged between the front-end master lens and the rear-end photoreceptor and including multiple microlenses.

2. The dental endoscope of claim 1, wherein each camera unit comprises two cameras and relative positions of the two cameras are calibrated.

3. The dental endoscope of claim 1, wherein each camera unit comprises a camera array including multiple cameras, and relative positions of the multiple cameras are calibrated.

4. The dental endoscope of claim 1, wherein the image acquisition module further comprises surface structured light projection units which are in one-to-one correspondence with the camera units.

5. The dental endoscope of claim 1, wherein the housing is ellipsoid-shaped, or cylinder-shaped where end faces at two ends are camber surfaces, or rounded-corner-column-shaped where end faces at two ends are camber surfaces.

6. The dental endoscope of claim 5, wherein:
the housing comprises two end faces arranged oppositely, and a side face arranged between the two end faces, and the side face comprises two first side faces arranged oppositely and two second side faces arranged oppositely; and
the image acquisition module comprises two pairs of first camera units, and the two pairs of first camera units are symmetrically arranged at two end parts, in a long axis direction, of the housing, two first camera units in each pair of first camera units are arranged back to back, and cameras of the two first camera units respectively face towards the two first side faces of the housing.

7. The dental endoscope of claim 6, wherein
the image acquisition module further comprises two second camera units, the two second camera units are distributed in a cross section of the housing in which a center of the housing is located, the two second camera units are arranged back to back, and cameras of the two second camera units respectively face towards the two second side faces of the housing.

8. The dental endoscope of claim 6, wherein the image acquisition module further comprises two third camera units which are symmetrically arranged at two end parts, in a long axis direction, of the housing, the two third camera units are arranged back to back, and cameras of the two third camera units respectively face towards the two end faces of the housing.

9. The dental endoscope of claim 1, wherein the master control module is further configured to receive image information acquired by the image acquisition module, at least add corresponding timestamp information of image acquisition and an identification of camera unit to the image information, and send the image information after adding the image information to the storage module for storage.

10. The dental endoscope of claim 1, further comprising:
a power supply module, electrically connected with the image acquisition module, the wireless communication module, the master control module and the storage module, and configured to supply power to the image acquisition module, the wireless communication module, the master control module and the storage module; and
a switch module configured to control on and off states of a circuit by which the power supply module supplies power to each electric module, wherein the switch module comprises a magnetic switch unit.

11. The dental endoscope of claim 10, further comprising a wireless charging module.

12. The dental endoscope of claim 11, further comprising a base arranged independent of the housing;
wherein the base comprises a magnetic switch driving module configured to drive the magnetic switch unit to perform on and off actions and a wireless power transmission module matched with the wireless charging module.

13. The dental endoscope of claim 11, further comprising:
a stretching part, arranged outside the housing, having one end connected with the housing, wherein the stretching part comprises a connector having one end connected with the housing, and a handle connected with another end of the connector.

14. The dental endoscope of claim 13, wherein the connector is a drawstring or a connecting rod.

15. The dental endoscope of claim 13, wherein:
the wireless communication module, the master control module, the storage module, the power supply module, the switch module and the wireless charging module are all arranged in the handle;
the connector comprises an electrical connecting line; and
the image acquisition module and the modules in the handle perform data communication and power transmission through the electrical connecting line.

16. The dental endoscope of claim 1, wherein the housing comprises a probe part and a handheld part.

17. The dental endoscope of claim 16, wherein the probe part and the handheld part define at least a portion of an integrated structure.

18. The dental endoscope of claim 16, wherein the image acquisition module is arranged in the probe part.

19. The dental endoscope of claim 18, wherein the image acquisition module comprises two camera units which are arranged back to back, and two illumination units which respectively provide illumination to the two camera units.

20. The dental endoscope of claim 16, wherein the wireless communication module, the master control module and the storage module are all arranged in the handheld part.

21. The dental endoscope of claim 1, wherein the master control module is further configured to:
send a handshake message to the external device through the wireless communication module according to a first preset period, and determine that a response message to the handshake message returned by the external device is received within a first preset time duration, wherein the handshake message at least comprises a device identification of the dental endoscope; and receive a user authentication passed message sent by the external device, wherein the user authentication passed message is sent by the external device when the external device determines that the user authentication has passed according to the device identification of the dental endoscope in the handshake message and a mapping relationship between device identification and user identity.

\* \* \* \* \*